United States Patent [19]

Olken et al.

[11] Patent Number: 4,996,388

[45] Date of Patent: Feb. 26, 1991

[54] SEPARATION OF ETHYLTOLUENE ISOMERS

[75] Inventors: Michael M. Olken; Guo-shuh J. Lee; Juan M. Garces, all of Midland, Mich.

[73] Assignee: The Dow Chemical Company, Midland, Mich.

[21] Appl. No.: 558,355

[22] Filed: Jul. 26, 1990

[51] Int. Cl.$^5$ .............................................. C07C 7/13
[52] U.S. Cl. ................................ 585/828; 208/310 R; 208/310 Z; 585/820; 585/826
[58] Field of Search ...................... 108/310 R, 310 Z; 585/822, 826, 828

*Primary Examiner*—Curtis R. Davis
*Assistant Examiner*—William Diemler

[57] ABSTRACT

A process of separating the ortho, meta and para isomers of ethyltoluene. One aspect employs a ferrierite adsorbent which separates the para isomer from a mixture of the same and at least one of the meta and ortho isomers. A second aspect employs a silicalite adsorbent which separates the ortho isomer from a mixture of the same and the meta isomer. A third aspect combines the ferrierite and silicalite adsorbents in sequence to separate a mixture of the ortho, meta and para isomers into the essentially pure compounds.

22 Claims, No Drawings

SEPARATION OF ETHYLTOLUENE ISOMERS

BACKGROUND OF THE INVENTION

This invention pertains to the separation of the ortho, meta and para isomers of ethyltoluene.

The industrial utility of ethyltoluenes is well-known. Pure p-ethyltoluene, as well as mixtures of para and meta ethyltoluene, are precursors to the corresponding vinyltoluenes, which are useful as cross-linking agents in coating applications. o-Ethyltoluene is a useful starting material in preparing intermediates for chemical and pharmaceutical syntheses.

Typically, dialkyl-substituted, monocyclic aromatic hydrocarbons, such as ethyltoluene, are prepared by direct alkylation of benzene which yields a mixture of the three familiar isomers: ortho, meta, and para. Separation of these isomers is complicated by the fact that they typically have similar melting and boiling points. For example, the boiling points of ortho, meta, and para ethyltoluene are 164°–165° C., 158°–159° C., and 162° C., respectively. Thus, a distillation column designed to separate a mixture of these isomers is required to have a large number of plates, and even then the separation is inefficient. The fractional distillation of ortho, meta and para ethyltoluenes, for example, yields ortho-para and meta-para mixtures.

It is known in the art to separate the isomers of dialkyl-substituted, monocyclic aromatic hydrocarbons having eight or nine carbon atoms by the use of zeolite adsorbents. U.S. Pat. No. 3,699,182 discloses the use of aluminosilicate ZSM-5 and ZSM-8 zeolites for the separation of a mixture of para xylene from a mixture of the same with ortho xylene and/or meta xylene. It is also illustrated that mixtures of 2- and 4-ethyltoluenes can be separated. Disadvantageously, these adsorbents do not separate all three isomers of the above-identified $C_8$ and $C_9$ aromatic hydrocarbons.

U.S. Pat. No. 4,376,226 teaches the use of crystalline aluminosilicate adsorbent CSZ-1 for the separation of a $C_8$, $C_9$ or $C_{10}$ aromatic feedstream. The adsorbent is applicable to a mixture of ethyltoluenes: however, the separation is not particularly effective. As a further disadvantage, the adsorbent contains a high concentration of aluminum which introduce acidic sites which may catalyze undesirable side reactions, such as isomerization and cracking.

U.S. Pat. No. 4,482,777 discloses a process for separating the ortho-isomer from a feed mixture comprising at least two bialkyl substituted monocyclic aromatic isomers of $C_8$ to $C_{18}$ carbon atoms, including the orthoisomer. The adsorbent is a crystalline aluminosilicate zeolite of the X or Y class. Disadvantageously, this process is not particularly efficient, since mixtures of the ortho and para isomers and the ortho and meta isomers are obtained. Even more disadvantageously, zeolite X has limited thermal stability. As a further disadvantage, the adsorbent contains a high concentration of aluminum which introduce acidic sites which may atalyze undesirable side reactions, such as isomerization and cracking.

Other aluminosilicate adsorbents are known for the separation of the above-identified alkylaromatic hydrocarbons, including zeolite beta as described in U.S. Pat. No. 4,554,398. Despite the advances made in the art, however, a need exists for the improvement of such isomer separations. What is needed is a simple process of separating ethyltoluene isomers which does not require expensive and complicated engineering, such as large distillation columns. What is also needed is a clean separation process which does not produce undesirable by-products. Most needed, however, is a simple and clean separation process having a high degree of efficiency such that essentially pure ortho, meta and para ethyltoluene isomers are obtained.

SUMMARY OF THE INVENTION

In one aspect this invention is a process of separating the para isomer from a mixture of the same and at least one of the ortho and meta isomers of ethyltoluene comprising (a) passing a feedstream containing the para isomer and at least one of the ortho and meta isomers of ethyltoluene through an adsorbent bed comprising ferrierite under conditions such that the ortho and/or meta isomers are not significantly adsorbed, while the para isomer is selectively adsorbed, (b) collecting the ortho and/or meta isomers leaving the adsorbent bed, and (c) removing the para isomer from the adsorbent by varying the conditions of the adsorbent bed such that the para isomer is substantially removed.

In another aspect this invention is a process of separating ortho ethyltoluene from a mixture of the same and meta ethyltoluene comprising (a) passing a feedstream containing the ortho and meta isomers of ethyltoluene, the feedstream being essentially free of para ethyltoluene, through an adsorbent bed comprising silicalite under conditions such that the ortho isomer is not significantly adsorbed, while the meta isomer is selectively adsorbed, (b) collecting the ortho isomer leaving the adsorbent bed, and (c) removing the meta isomer from the adsorbent bed by varying the conditions of the adsorbent bed such that the meta isomer is substantially removed.

In a third aspect, this invention is a process of separating a mixture of the ortho, meta and para isomers of ethyltoluene comprising (a) contacting a mixture of the ortho, meta and para isomers of ethyltoluene with a first adsorbent bed comprising ferrierite under conditions such that the ortho and meta isomers are not significantly adsorbed while the para isomer is selectively adsorbed, (b) collecting a mixture of the ortho and meta isomers leaving the adsorbent bed, (c) removing the para isomer from the first adsorbent bed by varying the conditions of the adsorbent bed such that the para isomer is removed, (d) contacting the mixture of the ortho and meta isomers with a second adsorbent bed comprising silicalite under conditions such that the ortho isomer is not significantly adsorbed while the meta isomer is selectively adsorbed, (e) collecting the ortho isomer, and (f) removing the meta isomer from the second adsorbent bed by varying the conditions in the bed such that the meta isomer is removed.

The separation processes of this invention are advantageous because they are simple and do not require complicated and expensive process equipment. More advantageously, the two processes of this invention employing the silicalite and ferrierite adsorbents separately can be combined into a third process which provides the ortho, meta and para isomers of ethyltoluene in essentially pure form. As a further advantage, the silicalite adsorbent of this invention does not contain a significant concentration of aluminum. Consequently, this adsorbent is less acidic than aluminosilicate adsorbents, and accordingly the process of this invention employing silicalite does not produce significant cracking or isomerization by-products.

DETAILED DESCRIPTION OF THE INVENTION

The following definitions will be useful in understanding the discussion which follows hereinbelow. The term "feedstream" is taken to mean a mixture containing two or more isomers which are fed to an adsorbent in any one of the processes of this invention. The term "extract component" is taken to mean an isomer that is more selectively adsorbed by the adsorbent, while a "raffinate component" is an isomer that is less selectively adsorbed. The term "raffinate stream" means a carrier stream through which a raffinate component is removed from an adsorbent. The term "desorbent component" is taken to mean a material capable of desorbing an extract component. The term "desorbent stream" means a stream through which an extract component has been desorbed and removed from the adsorbent, such as by the use of a desorbent component or by varying the conditions of the adsorbent bed.

The feedstreams which are acceptable for the processes of this invention comprise two or more of the isomers of ethyltoluene. For the separation of the ortho and meta isomers over silicalite adsorbent, only a feedstream containing the ortho and meta isomers can be employed, and the feedstream must be essentially free of para ethyltoluene. By "essentially free" is meant that the concentration of para ethyltoluene is less than about 5 mole percent, preferably less than about 3 mole percent, most preferably less than about 1 mole percent. It has been found that the para isomer is strongly adsorbed by silicalite; therefore, this adsorbent can be poisoned by the presence of too much para isomer. If at any time the bed is so poisoned, the bed can be regenerated by use of a desorbent and by varying the temperature and pressure of the bed such that the para isomer is removed. For the separation of the para isomer over ferrierite adsorbent, mixtures of the ortho and para isomers, or the meta and para isomers, or a mixture of all three isomers are suitable. In the third aspect of this invention combining both adsorbents in series, the feedstream comprises a mixture of the ortho, meta and para isomers.

The processes of this invention employ two adsorbents which may be used independently or in combination. The first adsorbent is a crystalline aluminosilicate molecular sieve known as "ferrierite," which occurs in nature and can also be synthesized. Ferrierites have the following composition in terms of oxides:

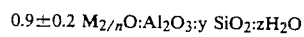

$0.9 \pm 0.2\ M_{2/n}O:Al_2O_3:y\ SiO_2:zH_2O$ wherein M is at least one cation of valence n, preferably an alkali or alkaline earth metal ion, y is between about 2 and about 150, preferably between about 6 and about 50, and z is between about 0 and about 200, preferably between about 0 and 120. Ferrierite occurs in an orthorhombic symmetry classifying into the crystallographic space group Immm. The pore system comprises two-dimensional channels parallel to the c and b axes. The larger pores contain 10-rings and are elliptical in cross-section with dimensions 4.3Å by 5.5Å. The smaller pores contain 8-rings and are also elliptical in cross-section with dimensions 3.4Å by 4.8Å. Ferrierites are further described by D. W. Breck in "Zeolite Molecular Sieves," John Wiley & Sons, 1974, at pages 127, 146, 219 and 358, incorporated herein by reference.

In the first aspect of this invention ferrierite is employed to separate the para isomer of ethyltoluene from a feed mixture containing the same and at least one of the ortho and meta isomers of ethyltoluene.

The second adsorbent employed in the process of this invention is a crystalline silica molecular sieve known as "silicalite." Silicalite is a polymorph of $SiO_2$ and is essentially "aluminum-free." The crystalline structure of silicalite is indicative of space group Pnma or $Pn2_1a$ and is similar to that of the aluminosilicate zeolite ZSM-5. Silicalite possesses a three-dimensional pore system composed of near-circular zig-zag channels along the a axis cross-linked by elliptical, straight channels along the b axis. Both channels are defined by 10-rings. Silicalite is also hydrophobic and organophilic, and therefore selectively adsorbs organic molecules over water. The identifying features of silicalite are more thoroughly discussed in U S. Pat. No. 4,061,724 and by E. M. Flanigen et al. in "Silicalite: A New Hydrophobic Crystalline Silica Molecular Sieve," Nature, 271. Feb. 2, 1978, which are incorporated herein by reference.

Whereas ZSM-5 contains a significant amount of aluminum, silicalite does not. It is known that aluminum is associated with acidic sites, and further that acidic sites are reactive in undesirable cracking and isomerization reactions. Accordingly, silicalite functions as a molecular sieve, but advantageously is less reactive than the crystallographically similar ZSM-5 aluminosilicate. Moreover, unlike aluminum-containing zeolites silicalite does not exhibit cation-exchange properties.

In a second aspect of this invention silicalite is employed to separate the ortho isomer of ethyltoluene from a feed mixture containing the ortho and meta isomers of ethyltoluene.

In a preferred embodiment, the ferrierite and silicalite adsorbents are combined in a sequential fashion, and employed to separate a feed mixture comprising the ortho, meta and para isomers of ethyltoluene. The sequential ordering of the adsorbents is critical. Thus, the feed mixture comprising ortho, meta and para ethyltoluenes is passed through a first adsorbent bed of ferrierite to yield a first raffinate stream enriched in the meta and ortho isomers and a first desorbent stream enriched in the para isomer. The first raffinate stream is then passed through a second adsorbent bed of silicalite to yield a second raffinate stream enriched in the ortho isomer and a second desorbent stream enriched in the meta isomer. By such a process the isomers of ethyltoluene can be separated into essentially pure fractions.

The crystalline silicalite or ferrierite adsorbents can be employed as binderless aggregates, or they can be bound into aggregates or extrudate with binders known to those skilled in the art, such as silica, alumina, kaolin, or the like. Preferably, the adsorbent is prepared into extrudate with a binder of silica.

The feedstreams of the processes of this invention can be applied to the solid adsorbent beds in the gaseous or liquid phases. Preferably, the feedstreams are gaseous.

The flow properties of the liquid or gaseous feedstreams in the adsorbent beds will depend upon the size of the adsorbent particles. It is usually desirable to have small particles which increase the turbulence and hold time of the feedstream around the adsorbent. However, if the particles are too small, they will be more densely packed. In such designs a higher pressure is required to ensure a positive flow through the bed, and a large pressure drop may occur from the inlet to the outlet of the bed. A proper balance is achieved preferably with extrudate having a particle size in the range from about 1/32 inch to about ¼ inch in diameter. More preferably, the particle size is in the range from about 1/16 inch to about ⅛ inch in diameter.

The processes of this invention are conducted in any conventional manner known to those skilled in the art of isomer separations. Typically, the adsorbent is employed in the form of a compact fixed bed which is alternately contacted with the feed mixture and desorbent materials. The feed mixture and desorbent materials may be applied in the liquid phase in an alternating fashion to the column, as in a typical chromatographic column. Alternatively, the feed mixture may be contacted in the gas phase with the solid adsorbent bed, and a raffinate stream may be collected until at least one extract component breaks through the adsorbent bed into the raffinate stream. At this point the feed stream is stopped, and the extract components are removed from the adsorbent bed by changing the temperature and/or pressure of the bed. This method is known in the art as the "temperature or pressure swing method" and is described by Ralph T. Yang in *Gas Separation by Adsorption Processes*, Butterworth, 1987, Chapters 6, 7, and 8. Optionally, a purge stream comprising an inert gas, such as nitrogen or helium, may be employed as a desorbent in the swing method to increase the rate of description of the extract components.

In the simplest embodiment of the invention the adsorbent is employed in the form of a static single bed in which case the process is only semi-continuous. In another embodiment a set of two or more static beds may be employed with appropriate valving, so that the feed mixture is passed through one or more adsorbent beds while simultaneously the desorbent materials can be passed through one or more of the other beds in the set. The flow of the feed mixture and desorbent materials may be either up or down through the adsorbent bed. Any conventional apparatus employed in static bed fluid-solid or gas-solid contacting may be used. Alternatively, the adsorbent may be employed in a moving bed system wherein the adsorption and description operations are continuously taking place, which allows both continuous production of a desorbent stream and a raffinate stream and the continual use of feed and desorbent streams. Such a system is described in U.S. Pat. No. 2,985,589, and is incorporated herein by reference.

A desorbent may be employed in the processes of this invention, if desired. Preferably, a desorbent is employed. The desorbent may be any liquid or gas which is non-reactive with the adsorbents and isomeric hydrocarbons, and which aids in desorbing the extract components from the adsorbent bed. Non-limiting examples of desorbents include alkanols, such as methanol and ethanol, and alkylamines, such as methylamine, as well as gases, such as nitrogen, helium, carbon dioxide and ammonia. Preferably, the desorbent is ammonia or methanol.

Any operable temperature is suitable for passing the feedstream and desorbent streams through the adsorbents, provided that these streams are in the liquid or gaseous state and not subject to decomposition. Preferably, the temperature for the processes of this invention ranges from about 100° C. to about 362° C., which is 200° C. above the average boiling point of the isomeric mixture. More preferably, the temperature ranges from about 162° C. to about 262° C. Below the lower preferred temperature the feedstream may not be sufficiently volatile. Above the upper preferred temperature the feedstream may decompose.

Any operable pressure is suitable for passing the feedstream and desorbent streams through the adsorbents provided that the feedstream is maintained in the liquid or gaseous state. The pressure will vary considerably depending upon the design and size of the reactor, the particle size of the adsorbent, the temperature of the bed, and whether the feedstream or the desorbent stream is being employed. Typically, the pressure will vary from subatmospheric to super-atmospheric. Preferably, the pressure will be in the range from about 7 psig to about 200 psig.

Any operable flow rate of the feedstreams an desorbent streams through the adsorbent beds is acceptable provided that the aforementioned separations of this invention are achieved. The flow rate will depend upon the size and configuration of the adsorbent bed and the desired purity of product. Generally, the flow rate can vary over a wide range from as low as a few cc/hr to as high as many thousands of liters/hr.

The composition of the raffinate stream can vary from almost 100 percent carrier to almost 100 percent raffinate component(s). Likewise if a desorbent component is employed, the composition of the desorbent stream can vary from essentially 100 percent desorbent component to essentially 100 percent extract component(s). Although it is possible by the processes of this invention to produce high purity extract components or raffinate components, it will be appreciated that an extract component is never completely adsorbed by the adsorbent, nor is a raffinate component completely non-adsorbed by the adsorbent. Therefore, small amounts of a raffinate component can appear in the desorbent stream, and likewise small amounts of an extract component can appear in the raffinate stream. The processes of this invention, however, achieve a high separation efficiency such that essentially pure fractions of the isomers are obtained. By "essentially pure" is meant an isomeric fraction that is at least about 95 mole percent pure, preferably at least about 97 mole percent pure, more preferably at least about 99 mole percent pure. Isomeric fractions obtained in the separations of this invention may be recycled through the ferrierite and silicalite adsorbent beds of this invention as often as desired to obtain fractions of increased purity.

Illustrative Embodiments

The following examples are illustrative of the processes of this invention, but are not intended to be limiting of the scope thereof.

EXAMPLE 1

Ferrierite aluminosilicate zeolite (Toyo Soda HTSZ 720-1X: 1.5 g) is packed into a stainless steel column (0.25 in. diameter ×6 in. length), and placed in a Hewlett Packard Model 5710 gas chromatograph set at the following conditions: carrier gas, helium: flow rate, 30 ml min$^{-1}$; inlet temperature, 300° C.; detector temperature 300° C.; oven temperature, 225° C. A mixture (0.5 μl) of the ortho, meta and para isomers of ethyltoluene in an o:m:p mole ratio of 1/1/1 is injected onto the column. One peak is observed at 0.26 minutes retention time: but no other significant peaks are found out to about 34 minutes retention time. A comparison of the observed peak with injections of the individual pure isomers indicates that the peak is a mixture of ortho and meta ethyltoluene. Para ethyltoluene has a greater affinity for the ferrierite column, and is retained for a time longer than 34 minutes.

EXAMPLE 2

Silicalite (Union Carbide S115, lot #9959-58; 1.5 g) is packed into a stainless steel column (0.25 in. diameter ×6 in. length), and placed in a Hewlett Packard Model 5710 gas chromatograph set at the following conditions: carrier gas, helium; flow rate, 30 ml min$^{-1}$; inlet temperature, 300° C.; detector temperature 300° C.; column temperature, 225° C. A mixture (2 μl) of the ortho and meta isomers of ethyltoluene in an o:m mole ratio of 1/1 is injected onto the column. One peak is observed at 0.13 minutes retention time: but no other significant peaks are found out to about 34 minutes retention time. A comparison of the observed peak with injections of the individual pure isomers indicates that the peak at 0.13 minutes is ortho-ethyltoluene. Meta-ethyltoluene has a greater affinity for the silicalite column, and is retained for a time longer than 34 minutes.

Examples 1 and 2 may be combined in series as an illustration of the third aspect of this invention wherein a mixture of ortho, meta and para ethyltoluenes is separated into three pure isomeric fractions. In such as an example, a mixture of ortho, meta and para ethyltoluenes is passed through a column of ferrierite to obtain the pure para isomer and a mixture of the ortho and meta isomers. The mixture of ortho and meta isomers is thereafter passed through the silicalite adsorbent to obtain the pure meta and ortho isomeric fractions.

What is claimed is:

1. A process for the separation of ortho-ethyltoluene from a mixture of the same and meta ethyltoluene comprising (a) passing a feedstream containing the ortho and meta isomers of ethyltoluene, the feedstream being essentially free of para ethyltoluene, through an adsorbent bed comprising silicalite under conditions such that the ortho isomer is not significantly adsorbed, while the meta isomer is selectively adsorbed, (b) collecting the ortho isomer leaving the adsorbent bed, and (c) removing the meta isomer from the adsorbent bed by varying the conditions of the adsorbent bed such that the meta isomer is substantially removed.

2. The process of claim 1 wherein a binder for the silicalite is employed.

3. The process of claim 1 wherein the isomeric mixture is in the gas phase.

4. The process of claim 1 wherein the adsorbent bed temperature is in the range from about 100° C. to about 362° C.

5. The process of claim 1 wherein the temperature and pressure swing method is employed.

6. A process of separating para-ethyltoluene from a mixture of the same and at least one of the ortho and meta isomers of ethyltoluene comprising (a) passing a feedstream containing the para isomer and at least one of the ortho and meta isomers of ethyltoluene through an adsorbent bed comprising ferrierite under conditions such that the ortho and/or meta isomers are not significantly adsorbed, while the para isomer is selectively adsorbed, (b) collecting the ortho and/or meta isomers leaving the adsorbent bed, and (c) removing the para isomer from the adsorbent by varying the conditions of the adsorbent bed such that the para isomer is substantially removed.

7. The process of claim 6 wherein the mixture contains the ortho and para isomers.

8. The process of claim 6 wherein the mixture contains the para and meta isomers.

9. The process of claim 6 wherein the mixture contains the ortho, meta and para isomers.

10. The process of claim 6 wherein a binder is employed with the ferrierite.

11. The process of claim 6 wherein the isomeric mixture is in the gas phase.

12. The process of claim 6 wherein the adsorbent bed temperature is in the range from about 162° C. to about 362° C.

13. The process of claim 6 wherein the temperature and pressure swing method is employed.

14. A process comprising (a) contacting a mixture of the ortho, meta and para isomers of ethyltoluene with a first adsorbent bed comprising ferrierite under conditions such that the ortho and meta isomers are not significantly adsorbed while the para isomer is selectively adsorbed, (b) collecting a mixture of the ortho and meta isomers leaving the adsorbent bed, (c) removing the para isomer from the first adsorbent bed by varying the conditions of the adsorbent bed such that the para isomer is removed, (d) contacting the mixture of the ortho and meta isomers with a second adsorbent bed comprising silicalite under conditions such that the ortho isomer is not significantly adsorbed while the meta isomer is selectively adsorbed, (e) collecting the ortho isomer, and (f) removing the meta isomer from the second adsorbent bed by varying the conditions in the bed such that the meta isomer is removed.

15. The process of claim 14 wherein a binder is employed with the adsorbents.

16. The process of claim 15 wherein the binder is silica.

17. The process of claim 14 wherein the isomeric mixture is in the gas phase.

18. The process of claim 14 wherein the adsorbent bed temperature is in the range from about 162° C. to about 362° C.

19. The process of claim 14 wherein the temperature and pressure swing method is employed.

20. The process of claim 14 wherein the particle size of the adsorbents is in the range from about 1/32 inch to about 2 inches in diameter.

21. The process of claim 14 wherein a desorbent is employed.

22. The process of claim 21 wherein the desorbent is ammonia or methanol.

* * * * *